United States Patent
Micoine et al.

(10) Patent No.: US 9,000,223 B2
(45) Date of Patent: Apr. 7, 2015

(54) PROCESS FOR PREPARING KETONES FROM EPOXIDES

(71) Applicants: Kevin Micoine, Oer-Erkenschwick (DE); Martin Roos, Haltern am See (DE); Peter Hannen, Herten (DE); Harald Haeger, Luedinghausen (DE); Klaus Bartosch, Haltern am See (DE)

(72) Inventors: Kevin Micoine, Oer-Erkenschwick (DE); Martin Roos, Haltern am See (DE); Peter Hannen, Herten (DE); Harald Haeger, Luedinghausen (DE); Klaus Bartosch, Haltern am See (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/192,269

(22) Filed: Feb. 27, 2014

(65) Prior Publication Data

US 2014/0249331 A1    Sep. 4, 2014

(30) Foreign Application Priority Data

Mar. 1, 2013 (DE) .......................... 10 2013 203 470

(51) Int. Cl.
| | | |
|---|---|---|
| *C07C 45/57* | (2006.01) | |
| *C07C 45/58* | (2006.01) | |
| *B01J 23/38* | (2006.01) | |
| *B01J 21/06* | (2006.01) | |
| *B01J 23/42* | (2006.01) | |
| *B01J 23/44* | (2006.01) | |
| *B01J 23/46* | (2006.01) | |

(52) U.S. Cl.
CPC ................ *B01J 23/38* (2013.01); *C07C 45/58* (2013.01); *B01J 21/06* (2013.01); *B01J 23/42* (2013.01); *B01J 23/44* (2013.01); *B01J 23/462* (2013.01); *B01J 23/464* (2013.01); *B01J 23/466* (2013.01); *B01J 23/468* (2013.01); *C07C 2101/20* (2013.01)

(58) Field of Classification Search
CPC .... C07C 45/57; C07C 45/513; C07C 2101/14
USPC .................................................... 568/341, 361
See application file for complete search history.

(56) References Cited

U.S. PATENT DOCUMENTS 6,515,185 B1 * 2/2003 Kuroda et al. ................ 568/338
2002/0107142 A1    8/2002 Yamazaki et al.

FOREIGN PATENT DOCUMENTS

| EP | 1 018 498 A2 | 7/2000 |
|---|---|---|
| EP | 1 090 900 A1 | 4/2001 |
| WO | WO 2012/166335 A1 | 12/2012 |
| WO | WO 2013/013704 A1 | 1/2013 |

OTHER PUBLICATIONS

V.S, Joshi, et al., "Organic Reactions in a Solid Matrix—II*" Tetrahedron, vol. 27, 1971, pp. 459-474.

F. A. Chernyshkove, et al., "Preparation of Cyclododecanone by Isomerization of Epoxycyclododecane Over Pd and Rh" Neftekhimiya, vol. 16, No. 2, 1976, pp. 250-254.

European Search Report issued Jun. 18, 2014 in Patent Application No. 14 15 4590 (with English translation of categories of cited documents).

Weizhen Li, et al., "Structures and properties of zirconia-supported ruthenium oxide catalysts for the selective oxidation of methanol to methyl formate", The Journal of Physical Chemistry B, vol. 110, No. 46, XP055123218, Nov. 1, 2006, pp. 23337-23342.

J.H. Bitter, et al., "The state of zirconia supported platinum catalysts for CO2/CH4 reforming", Journal of Catalysis, vol. 171, No. 1, XP004468804, Oct. 1, 1997, pp. 279-286.

Vinay Tiwari, et al., "One-step synthesis of noble metal-titanium dioxide nanocomposites in a flame aerosol reactor", Applied Catalysis A: General, vol. 345, No. 2, XP022808078, Aug. 1, 2008, pp. 241-246.

* cited by examiner

*Primary Examiner* — Sikarl Witherspoon
(74) *Attorney, Agent, or Firm* — Oblon, McClelland, Maier & Neustadt, L.L.P.

(57) ABSTRACT

A process for preparing a ketone by conversion of a compound E which contains an epoxy group to the ketone in the presence of a mixture comprising at least one noble metal and at least one metal oxide as a catalyst system, wherein the metal oxide in the catalyst system is at least one of titanium dioxide and zirconium dioxide, and the process is conducted at 0 to 0.9 bar of hydrogen.

10 Claims, No Drawings

PROCESS FOR PREPARING KETONES FROM EPOXIDES

CROSS REFERENCE TO RELATED APPLICATIONS

This application claims priority to German Application No. 102013203470.9, filed Mar. 1, 2013, the disclosure of which is incorporated herein by reference in its entirety.

BACKGROUND OF THE INVENTION

The present invention relates to a process for preparing a ketone from an aliphatic or cycloaliphatic compound E containing at least one epoxy group, and to a process for synthesizing lactams.

The opening of oxirane rings with acidic or basic oxides has been described (V. S. Joshi, N. P. Damodaran, S. Dev, Tetrahedron 1971, 27, 459-474; K. Arata, K. Tanabe, Bull. Chem. Soc. Jpn. 1980, 53, 299-303; K. Arata, H. Nakamura, Y. Nakamura, Bull. Chem. Soc. Jpn. 1994, 67, 2351-2353). From a compound containing epoxy groups, such as monoepoxycyclododecane (CDAN epoxide), the allyl alcohol (3-cyclododecenol; CDENOL) may first be obtained. This may be followed by the conversion to the ketone (cyclododecanone; CDON).

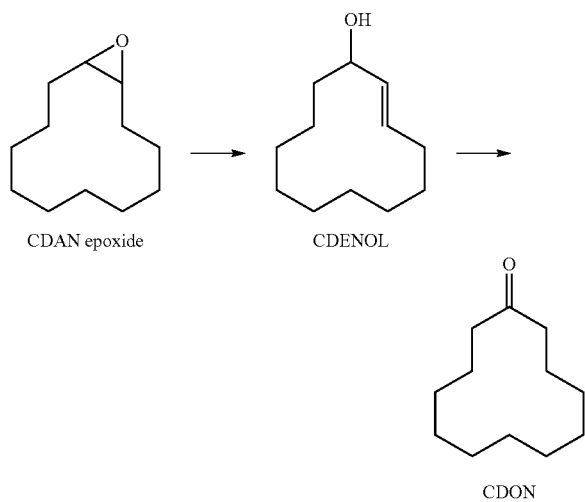

The problem which occurs in this two-stage reaction is that, as well as the cyclic allyl alcohol, dehydrated dienes or dimers form as by-products.

A selective conversion of the epoxide to the ketone was reported by Chemyshkove and Mushenko (Chemyshkove, F. A.; Mushenko, D. V. Neftekhimiya 1976, 16, 250-4). For this purpose, the epoxides were reacted in a hydrogen atmosphere over palladium and rhodium catalysts which were supported on alumina or carbon. With complete conversion of the reactant, the ketones were obtained with yields exceeding 80%.

EP-A-1090900 describes the reaction of CDAN epoxide to give a mixture of CDON and cyclododecanol (CDOL). For this purpose, platinum group metals, an inert support and a promoter are used. The reactions proceed in a hydrogen atmosphere.

EP-A-1018498 describes reaction of cyclic epoxides with hydrogen and platinum group metals in a hydrogen atmosphere to obtain a ketone/alcohol mixture. The hydrogen pressure is at least 1 bar. The document teaches that lower pressures would require an excessively long reaction time.

The problem thus addressed was that of adapting the production of ketones from epoxides such that a high proportion of ketone may be obtained with a low alcohol content. In addition, by-products, especially unsaturated by-products, should form in a minimum concentration. Moreover, the reaction should be of lower technical complexity in comparison to conventional methods previously described. The two-stage reaction to give the ketone should be possible without isolation of the intermediate allyl alcohol and the reaction time should correspond to the time required in conventional processes.

SUMMARY OF THE INVENTION

These and other objects are achieved according to the present invention, the first embodiment of which includes a process for preparing a ketone, comprising:
converting a compound E that comprises an epoxy group in the presence of a catalyst system to the ketone; wherein
the catalyst system comprises a noble metal and a metal oxide,
the metal oxide comprises at least one of titanium dioxide and zirconium dioxide, and a hydrogen pressure of the conversion is from 0 to 0.9 bar.

In a second embodiment according to the present invention the compound E is a cycloaliphatic compound. In a third embodiment the noble metal is selected from the group consisting of ruthenium, palladium and platinum. In a further embodiment of the present invention the catalyst system is selected from the group of systems consisting of system I, system II and system III, wherein in system I the noble metal is unsupported and the metal oxide comprises at least one of titanium dioxide and zirconium dioxide; in system II the noble metal is supported, the noble metal support does not comprise titanium dioxide or zirconium dioxide, and the system further comprises at least one of titanium dioxide and zirconium dioxide; and in system III the noble metal is supported on zirconium dioxide as the metal oxide.

In one special embodiment, the conversion is conducted without hydrogen.

In one further embodiment, the present invention provides a catalyst system comprising: a noble metal and a metal oxide, wherein the catalyst system is selected from the group of systems consisting of system I, system II and system III, wherein in system I the noble metal is unsupported and the metal oxide comprises at least one of titanium dioxide and zirconium dioxide; in system II the noble metal is supported, the noble metal support does not comprise titanium dioxide or zirconium dioxide, and the system further comprises at least one of titanium dioxide and zirconium dioxide; and in system III the noble metal is supported on zirconium dioxide as the metal oxide.

In one particular embodiment of the present invention the compound E is 1,2-cyclododecane epoxide.

DETAILED DESCRIPTION OF THE PREFERRED EMBODIMENTS

Throughout this description all ranges described include all values and sub-ranges therein, unless otherwise specified.

Additionally, the indefinite article "a" or "an" carries the meaning of "one or more" throughout the description, unless otherwise specified.

In a first embodiment, the present invention provides a process for preparing a ketone, comprising:

converting a compound E that comprises an epoxy group in the presence of a catalyst system to the ketone; wherein
the catalyst system comprises a noble metal and a metal oxide,
the metal oxide comprises at least one of titanium dioxide and zirconium dioxide, and a hydrogen pressure of the conversion is from 0 to 0.9 bar.

Zirconium dioxide is the preferred metal oxide.

The process according invention is conducted in the presence of a heterogeneous catalysis.

The compound E may be aliphatic or cycloaliphatic, preference being given to cycloaliphatic compounds. Preferably 4 to 20 carbon atoms, more preferably 6 to 16 carbon atoms, especially preferably 8 to 14 carbon atoms, very especially preferably 10 to 12 carbon atoms and especially 12 carbon atoms are present in the compound E.

The compound E may contain one or more epoxy groups, preference being given to monoepoxy compounds. In addition, the compound may be saturated or unsaturated. For example, one or two double bonds may be present.

Preferred compounds E are monoepoxycycloalkanes, monoepoxycyclo-alkanedienes and monoepoxycycloalkenes, particular preference being given to monoepoxycycloalkanes. A very particularly preferred compound E is monoepoxycyclododecane (CDAN epoxide).

It has been found that the formation of the corresponding alcohol as a by-product depends on the hydrogen pressure: with rising pressure, the alcohol content increases, and so the ketone selectivity decreases.

The process according to the invention may be conducted at a hydrogen pressure of up to 8 bar, the hydrogen pressure being set preferably to 0 to 5 bar and more preferably to 0 to 2.5 bar. The hydrogen pressure may preferably be 0 to 0.9 bar, very especially preferably 0 to 0.5 bar. The process according to the invention may be performed without hydrogen, but it may be preferable to initially charge at least a low hydrogen content to suppress unsaturated by-products. This may be 0.05 to 0.5 bar, preferably 0.1 to 0.4 bar.

A process without hydrogen or with a hydrogen pressure of not more than 0.9 bar may be advantageous for catalyst systems comprising titanium dioxide.

The pressure figures given above are based on the partial pressure of hydrogen in the system. Typically, components of the reaction mixture, including the solvent, air or inert gases such as nitrogen or argon, are further gaseous constituents of the system.

By virtue of the low hydrogen pressures, the process of the present invention may be of a much lower level of technical complexity in comparison to the conventionally known processes described previously. This effect may be especially evident with regard to the suitable apparatus, for being able to work with hydrogen. A particular advantage of the invention may be that the ketone can be obtained in high yields without the presence of hydrogen.

The temperature during the reaction may preferably be from 100 to 350° C., preferably 175 to 275° C. and more preferably between 200 and 250° C. The reaction may be conducted wherein compound E is in the liquid or gaseous state.

The noble metal in the catalyst system may preferably be selected from the group consisting of ruthenium, rhodium, palladium, osmium, iridium and platinum, with preference being given to ruthenium, palladium and platinum, and particular preference to palladium. The noble metal may be in the form of powder (unsupported) or in supported form. Elemental noble metals or oxides thereof, for example, may also be suitable in powder form.

In addition, at least one metal oxide may be present as a further constituent of the catalyst system. The metal oxide in the catalyst system comprises titanium dioxide, zirconium dioxide or mixtures thereof, or consists of at least one of the aforementioned oxides. These also include titanium dioxide- or zirconium dioxide-doped or -coated substances such as alumina or silica.

The metal oxide in the catalyst system may function as a support for the noble metal in the catalyst system. The noble metal may optionally be applied to an alternative support selected, for example, from alumina, silica or activated carbon. Titanium dioxide or zirconium dioxide may be preferred supports.

The metal oxides in the catalyst system and the alternative supports may be in the form of powders or shaped bodies. Suitable shaped bodies are spheres, extrudates, tablets, granules and pellets. It is preferable that the supports of the noble metal are in the form of shaped bodies. It is likewise preferable that the metal oxide in the catalyst system, if it does not function as a support, is in the form of shaped bodies.

Irrespective of whether or not the noble metal is supported and which support is used, it is essential to the invention that at least one metal oxide is present in the catalyst system.

The catalyst system may consequently independently be present as one of the following system forms:

I) The noble metal is unsupported; the metal oxide present in the catalyst system is at least titanium dioxide or zirconium dioxide;

II) the noble metal is supported, where the support does not comprise or consist of titanium dioxide and/or zirconium dioxide. The system additionally comprises at least one metal oxide selected from titanium dioxide and zirconium dioxide.

III) The noble metal is supported on a metal oxide selected from titanium dioxide and zirconium dioxide.

System forms II and III are preferred, system form III being particularly preferred.

Suitable titanium dioxide as a metal oxide in the catalyst system may be obtained by the sulphate process, the chloride process, or by flame hydrolysis (pyrogenic process) of titanium tetrachloride. All the processes are known to those skilled in the art. Suitable polymorphs are rutile and anatase, and the titanium dioxide used may comprise mixtures of the polymorphs mentioned.

The titanium dioxide prepared by the sulphate or chloride process may give an acidic reaction in water, the compounds typically having a pH of 3 or less (acidic titanium dioxide). Acidic titanium dioxide likewise usually contains more than 5% by weight, based on the total weight of the titanium dioxide support, of substances such as titanyl sulphate or titanyl hydroxide. A titanium dioxide based on an acidic titanium dioxide is commercially available as Aerolyst 7750 (Evonik, Germany). Acidic titanium oxide is less preferred for the present process. In other words, it is preferable not to use acidic titanium dioxide. Suitable nonacidic titanium dioxide, which may be preferred, exhibits a pH of 5 or more in water.

Particularly preferred titanium dioxide is obtained by flame pyrolysis, as described, for example, in DE-A-830786.

Suitable titanium dioxide is obtainable under the Aeroxide P25 titanium dioxide (powder) or Aerolyst 7711 (shaped bodies) name from Evonik, Germany, and Hombikat M234 (shaped bodies) from Sachtleben, Germany.

Zirconium dioxide (zirconium(IV) oxide) is obtainable, for example, from zirconium hydroxide, by calcining it at more than 200° C., for example at 350° C. The zirconium dioxide may be doped, for example, with yttrium oxide.

Suitable zirconium dioxide is monoclinic or tetragonal. Mixtures of these polymorphs are possible.

The metal oxide in the catalyst system may have an average bulk density of 0.5 to 2 g/cm$^3$.

The metal oxide in the catalyst system may have a BET surface area of at least 5 m$^2$/g.

The proportion of noble metal, based on the total weight of noble metal and support, may be 0.01 to 5% by weight, preferably 0.05 to 1.2% by weight and more preferably 0.1 to 0.6% by weight.

The noble metal may be distributed on or within the support.

The molar proportion of noble metal, based on the molar amount of the compound E, may be 0.00001 to 0.1, preferably 0.0001 to 0.01.

The molar proportion of metal oxide in the catalyst system, based on the molar amount of the compound E, may be 0.01 to 100, preferably 0.01 to 10.

The process according to the invention may be conducted in organic solvents, though it is preferable to work without solvents and hence not to use any organic solvent. Suitable solvents are, for example, alkanes such as n-hexane, n-heptane, n-tetradecane and cyclohexane; ethers such as tetrahydrofuran and dioxane; alkanols such as methanol, ethanol and t-butanol; esters such as ethyl acetate and butyl acetate. The solvents themselves may be used alone or in mixtures. The solvent is preferably used in an amount of 20 times or less, preferably 10 times or less, the weight of the compound E.

The process according to the invention can be executed continuously or batchwise.

The ketone can be purified by distillation, crystallization or recrystallization.

It may be preferable that the process according to the invention is performed without a promoter component. The promoter component may be a member which is selected from the elements of group VIII, of group Ib, of group IIb, of group IIIb, of group IVb, of group Vb, of group VIb and of group VIIb, lanthanide elements, and compounds of the aforementioned elements. Corresponding promoter components are described in EP-A-1090900. The aforementioned metal oxides in the catalyst system or alternative supports are not regarded as promoter components.

In a preferred embodiment of the invention, CDAN epoxide is converted to CDON without solvent at temperatures of 200 to 250° C., the catalyst used being a palladium-zirconium dioxide having a palladium content of 0.1 to 0.6% by weight, based on the total weight of the catalyst. In the reaction, a maximum of 0.9 bar of hydrogen, most preferably a maximum of 0.5 bar, is used.

The invention further comprises a catalyst system comprising noble metal and metal oxide, wherein I) the noble metal is unsupported; the metal oxide present in the catalyst system is at least titanium dioxide or zirconium dioxide;

II) the noble metal is supported, and wherein the support does not comprise or consist of titanium dioxide and/or zirconium dioxide; the system additionally comprises at least one metal oxide selected from titanium dioxide and zirconium dioxide;

III) the noble metal is supported on a metal oxide selected from titanium dioxide and zirconium dioxide.

In catalyst system III, zirconium dioxide may be preferred.

The invention further provides for the use of at least one inventive catalyst system for catalysis of a reaction in which at least one compound E is converted to the corresponding ketone derivative.

The invention further provides a process for synthesizing lactams (inventive lactam process), in which the aforementioned process according to the invention for preparing ketones is employed. The compound E may preferably be selected from aliphatic monoepoxycycloalkanes, aliphatic monoepoxycycloalkane-dienes and aliphatic monoepoxycycloalkenes, preference being given to monoepoxycycloalkanes.

If the ketone is in a mixture with the corresponding alcohol derivative, the alcohol can be dehydrogenated to the ketone. Subsequently, the ketone can be oximated. In the next step, the Beckmann rearrangement to give the lactam can be effected, in which case the rearrangement can be effected by means of sulphuric acid or cyanuric chloride. The lactams can be processed further by polycondensation to give polyamides.

The dehydrogenation, the oximation, the Beckmann rearrangement and the condensation reaction are known to those skilled in the art.

In a preferred embodiment of the inventive lactam process, laurolactam is prepared from monoepoxycyclododecane (i.e. cyclododecane epoxide or 1,2-cyclododecane epoxide).

In the context of the preferred lactam process, cyclododecane epoxide can be obtained by the following reaction steps: 1,3-butadiene is converted by cyclotrimerization to cyclododecatriene. This is followed by hydrogenation to give the cyclododecene. Subsequent epoxidation gives the cyclododecane epoxide. The person skilled in the art in the field of synthesis of organic compounds can prepare other aliphatic and cycloaliphatic compounds E in analogy to the synthesis of cyclododecane epoxide.

Even without any further details, it is assumed that a person skilled in the art can utilize the above description to the broadest extent. The preferred embodiments and examples should therefore be regarded merely as descriptive disclosure which is not limiting in any way whatsoever.

Having generally described this invention, a further understanding can be obtained by reference to certain specific examples which are provided herein for purposes of illustration only, and are not intended to be limiting unless otherwise specified.

EXAMPLES

The percentage figure in the case of catalysts indicates the proportion by weight of the noble metal based on the total weight of the catalyst including noble metal and support. The abbreviation "calc." stands for "calcined". The abbreviations for the substances are: CDAN: cyclododecane; CDEN: cyclododecene; ECD: epoxycyclododecane; CDON: cyclododecanone; CDOL: cyclododecanol; CDENOL: cyclododecen-3-ol.

Example 1

Alumina Support (Conventional Method)

The reaction was conducted in a mechanically stirred 500 ml round-bottom flask. The reactor was heated with an electrical aluminium heating block and the internal temperature was monitored with a temperature sensor. The flask was charged with 50 ml of 1,2-cyclododecane epoxide and 10 g of catalyst, supported on alumina in the form of shaped bodies. The catalyst bed lay on the base of the flask and the liquid reaction mixture was stirred over the bed. The flask was subsequently inertized with nitrogen and heated to internal temperature 215° C. The temperature was maintained over 5 hours.

TABLE 1

| Catalyst | Support | Conversion (%) | Selectivity (%) | | | | |
|---|---|---|---|---|---|---|---|
| | | | CDAN | CDEN | CDON | CDOL | CDENOL |
| Ru/Al$_2$O$_3$ 1.5% | γ-Al$_2$O$_3$ | 99 | 0.2 | 5 | 71 | 7 | 1.3 |
| Pd/Al$_2$O$_3$ 0.5% | γ-Al$_2$O$_3$ | 100 | 1 | 4 | 75 | 6 | 0 |

Example 2

Various Metals and Supports (Inventive)

The reaction was conducted in a mechanically stirred 500 ml round-bottom flask. The reactor was heated with an electrical aluminium heating block and the internal temperature was monitored with a temperature sensor. The flask was charged with 50 ml of 1,2-cyclododecane epoxide and 10 g of catalyst system III (noble metal supported on titanium dioxide or zirconium dioxide, each in the form of shaped bodies). The catalyst bed lay on the base of the flask and the liquid reaction mixture was stirred over the bed. The flask was subsequently inertized with nitrogen and heated to internal temperature 215° C. The temperature was maintained over 5 hours.

TABLE 2

| Catalyst | Support | Conversion (%) | Selectivity (%) | | | | |
|---|---|---|---|---|---|---|---|
| | | | CDAN | CDEN | CDON | CDOL | CDENOL |
| Ru/TiO$_2$ 1.0% | Aerolyst® 7711 | 89 | 0 | 3 | 86 | 4 | 0.6 |
| Pd/TiO$_2$ 0.5% | Aerolyst® 7711 | 93 | 0.4 | 1 | 90 | 3 | 0 |
| Pd/ZrO$_2$ 0.5% | from Zr(OH)$_4$ 350° C. calc. | 90 | 0 | 0 | 96 | 3 | 0 |
| Pd/ZrO$_2$ 0.5% | t-ZrO$_2$, 8% Y$_2$O$_3$ | 94$^{(a)}$ | 0.2 | 0 | 94 | 3 | 0.3 |

$^{(a)}$30 g of catalyst and T = 235° C.

Example 3

Mixture of Catalysts (Inventive)

The reaction was conducted in a mechanically stirred 500 ml round-bottom flask. The reactor was heated with an electrical aluminium heating block and the internal temperature was monitored with a temperature sensor. The flask was charged with 50 ml of 1,2-cyclododecane epoxide, 10 g of supported noble metal (0.5% by weight of palladium on silica in the form of shaped bodies) and 10 or 20 g of metal oxide of the catalyst system (shaped bodies) (catalyst system II). The catalyst bed lay on the base of the flask and the liquid reaction mixture was stirred over the bed. The flask was subsequently inertized with nitrogen and heated to internal temperature 215° C. The temperature was maintained over 5 hours.

TABLE 3

| Catalyst (10 g) | Oxide | Conversion (%) | Selectivity (%) | | | | |
|---|---|---|---|---|---|---|---|
| | | | CDAN | CDEN | CDON | CDOL | CDENOL |
| Pd/SiO$_2$ 0.5% | —* | 7 | 0 | 0 | 97 | 0 | 0 |
| | 10 g TiO$_2$ Aerolyst® 7711 | >99 | 0.3 | 2 | 90 | 2 | 0 |

TABLE 3-continued

| Catalyst (10 g) | Oxide | Conversion (%) | Selectivity (%) | | | | |
|---|---|---|---|---|---|---|---|
| | | | CDAN | CDEN | CDON | CDOL | CDENOL |
| | 10 g $TiO_2$ Hombikat M234 | >99 | 0.6 | 12 | 77 | 0.7 | 0 |
| | 20 g m-$ZrO_2$ m-$ZrO_2$ | 68 | <0.1 | 0 | 98 | 1 | 0 |
| | 20 g $ZrO_2$ from $Zr(OH)_4$ 350° C. calc. | >99 | 0 | 0 | 95 | 3 | 0 |

*not in accordance with the invention

Example 4

Reaction with Full Conversion (Inventive)

The reaction was conducted in a mechanically stirred 500 ml round-bottom flask. The reactor was heated with an electrical aluminium heating block and the internal temperature was monitored with a temperature sensor. The flask was charged with 50 ml of 1,2-cyclododecane epoxide and catalyst (palladium on titanium dioxide in the form of shaped bodies or on zirconium dioxide in the form of shaped bodies; catalyst system III). The catalyst bed lay on the base of the flask and the liquid reaction mixture was stirred over the bed. The flask was subsequently inertized with nitrogen and heated to the desired internal temperature. The temperature was maintained over the given time until a full conversion of the epoxide was attained.

Example 5

Reaction with Various Hydrogen Pressures (Inventive)

The reaction was conducted in a 100 ml autoclave with a magnetic stirrer. The reactor was heated with a 200° C. oil bath. The autoclave was charged with 20 ml of 1,2-cyclododecane epoxide and 4 g of catalyst system III (palladium, supported on titanium dioxide powder (mortar-ground Aerolyst® 7711 support)). It was inertized with nitrogen, heated to the desired internal temperature and then pressurized with hydrogen up to the desired pressure. The oil temperature was maintained over 24 h.

TABLE 4

Composition (area %, GC) of the reaction mixture (5 h)

| Catalyst | Support | Temp. (° C.) | Time (h) | Yield (%) | | | | CDON + CDOL |
|---|---|---|---|---|---|---|---|---|
| | | | | CDAN | CDEN | CDON | CDOL | |
| 20 g Pd/$TiO_2$ 0.5% | Aerolyst® 7711 | 215 | 5 | 0.7 | 1.7 | 92.1 | 2.1 | 94.2 |
| 10 g Pd/$TiO_2$ 0.5% | Aerolyst® 7711 | 215 | 10* | 1.8 | 0 | 95.7 | 2.5 | 98.2 |
| 30 g Pd/$ZrO_2$ 0.5% | t-$ZrO_2$, with 8% by weight $Y_2O_3$ | 235 | 10 | 0.2 | 0 | 96.2 | 3.4 | 99.6 |
| 30 g Pd/$ZrO_2$ 0.5% | from $Zr(OH)_4$ 350° C. calc. | 235 | 5 | 0.5 | 0.5 | 93.5 | 5.5 | 99 |
| 10 g Pd/$ZrO_2$ 0.5% | from $Zr(OH)_4$ 350° C. calc. | 235 | 10 | 0.3 | 0.1 | 95.3 | 2.9 | 98.2 |

*$H_2/N_2$ mixture (1 bar with 90% by volume of $H_2$ and 10% by volume of $N_2$) was fed in during the last hour of the reaction.

TABLE 5

Composition (area %, GC) of the reaction mixture (5 h)

| Catalyst (4 g) | $H_2$ pressure (bar) | Conversion (%) | Selectivity (%) | | | | |
|---|---|---|---|---|---|---|---|
| | | | CDAN | CDEN | CDON | CDOL | CDENOL |
| Pd/ | 0 | 83 | 0.4 | 0 | 97 | 2 | 0 |
| $TiO_2$ | 3 | 91 | 0.8 | 0 | 87 | 12 | 0 |
| 0.5% | 5 | 94 | 1.6 | 0 | 67 | 31 | 0 |
| | 7 | 89 | 1.1 | 0 | 59 | 39 | 0 |

Example 6

Mixture of Pd Powder and $TiO_2$ (Inventive)

The reaction was conducted in a mechanically stirred 500 ml round-bottom flask. The reactor was heated with an electrical aluminium heating block and the internal temperature was monitored with a temperature sensor. The flask was charged with 50 ml of 1,2-cyclododecane epoxide, 10 g of $TiO_2$ powder and palladium(II) oxide powder as noble metal (catalyst system I). The catalyst bed lay on the base of the flask and the liquid reaction mixture was stirred over the bed. The flask was subsequently inertized with nitrogen and heated to internal temperature 215° C. The temperature was maintained over 5 hours.

TABLE 6

Composition (area %, GC) of the reaction mixture (5 h)

| Metal oxide | Noble metal | Conversion (%) | Selectivity (%) | | | | |
|---|---|---|---|---|---|---|---|
| | | | CDAN | CDEN | CDON | CDOL | CDENOL |
| —* | 0.12 g PdO (powder) | no conversion | | | | | |
| 10 g $TiO_2$ Aerolyst ® 7711 | none | 90 | 0 | 6 | 3 | 0 | 84 |
| 10 g $TiO_2$ Aerolyst ® 7711 | 0.12 g PdO powder | 79 | 0 | 5 | 46 | 0 | 22 |
| 10 g $TiO_2$ Aerolyst ® 7711 | 0.76 g PdO powder | 91 | 0 | 9 | 68 | 3 | 1 |

*not in accordance with the invention

Example 7

Reaction with $ZrO_2$ Powder (Inventive)

The reaction was conducted in a mechanically stirred 500 ml round-bottom flask. The reactor was heated with an electrical aluminium heating block and the internal temperature was monitored with a temperature sensor. The flask was charged with 50 ml of 1,2-cyclododecane epoxide and the catalyst system. The $Pd/SiO_2$ catalyst bed lay—where present—on the base of the flask. The liquid reaction mixture comprising $ZrO_2$ powder or Pd supported on $ZrO_2$ (powder) was stirred over the bed. The flask was subsequently inertized with nitrogen and heated to internal temperature 215° C. The temperature was maintained over 5 hours.

TABLE 7

Composition (area %, GC) of the reaction mixture (5 h)

| Catalyst system | Conversion (%) | Selectivity (%) | | | | |
|---|---|---|---|---|---|---|
| | | CDAN | CDEN | CDON | CDOL | CDENOL |
| 10 g Pd/ $SiO_2$ 0.5% (extrudate) + 20 g $ZrO_2$ (powder, 300° C. calcined) (system II) | >99 | 0 | 0 | 95 | 3 | 0 |
| 10 g Pd/ $SiO_2$ 0.5% (extrudate) + 10 g $ZrO_2$ (powder, 300° C. calcined) (system II) | 75 | 0 | 0 | 92 | 2 | 0 |
| 10 g Pd/ $ZrO_2$ 0.5% (powder, 300° C. calcined) (system III) | 75 | 0 | 0 | 96 | 2 | 0 |

Example 8

Continuous Process (Inventive)

The reaction was conducted in a continuously operated plant. The plant consisted of a fixed bed reactor (catalyst bed approx. 100 ml) and a steel reservoir vessel (1 l) with level measurement. The fixed bed reactor was charged with 100 g of $Pd/ZrO_2$ (0.5%; system III), and the vessel with 950 g of CDAN epoxide. The liquid was pumped in circulation from the reservoir through the catalyst bed and back into the reservoir vessel by means of a circulation pump (21 l/h). The reactor was heated to the desired internal temperature in the reaction mixture with an electrical heater. Once a conversion of 80% had been attained, fresh feed (CDAN epoxide) was metered into the plant. The product was discharged continuously from the plant, such that the fill level in the reservoir vessel remained constant. The reaction mixture was passed through the fixed bed and the vessel with nitrogen. The reaction was conducted without hydrogen (Table 8, line 1) and with hydrogen (partial pressure 0.25 bar; Table 8, line 2).

TABLE 8

| | | | | Composition (area %, GC) of the reaction mixture | | | | |
|---|---|---|---|---|---|---|---|---|
| | Temp | Feed | Conversion | | Selectivity (%) | | | |
| Pressure | (° C.) | (g/h) | (%) | CDAN + CDEN | CDON | CDOL | CDEN-ON | CDEN-OL |
| 1.1 bar $N_2$ 0 bar $H_2$ | 215 | 12 | 80.4 | 3.2 | 89 | 1.7 | 3.2 | 2.1 |
| 1.4 bar $N_2$ 0.25 bar $H_2$ | 205 | 34 | 84.7 | 9.2 | 84 | 5.1 | 0 | 0.1 |

Numerous modifications and variations on the present invention are possible in view of the above teachings. It is therefore to be understood that within the scope of the appended claims, the invention may be practiced otherwise than as specifically described herein.

The invention claimed is:

1. A process for preparing a ketone, comprising:
converting a compound E that comprises an epoxy group in the presence of a catalyst system to the ketone; wherein
the catalyst system comprises a noble metal and a metal oxide,
the metal oxide comprises at least one of titanium dioxide and zirconium dioxide, and
a hydrogen pressure of the conversion is from 0 to 0.9 bar.

2. The process according to claim 1, wherein the compound E is a cycloaliphatic compound.

3. The process according to claim 1, wherein the noble metal is selected from the group consisting of ruthenium, palladium and platinum.

4. The process according to claim 1, wherein the compound E comprises four to twenty carbon atoms.

5. The process according to claim 1, wherein the the hydrogen pressure is from 0 to 0.5 bar.

6. The process according to claim 1, wherein the catalyst system is selected from the group of systems consisting of system I, system II and system III,
wherein
in system I the noble metal is unsupported and the metal oxide comprises at least one of titanium dioxide and zirconium dioxide;
in system II the noble metal is supported, the noble metal support does not comprise titanium dioxide or zirconium dioxide, and the system further comprises at least one of titanium dioxide and zirconium dioxide; and
in system III the noble metal is supported on zirconium dioxide as the metal oxide.

7. The process according to claim 1, wherein the process is conducted without hydrogen.

8. A method to convert a compound E which comprises an epoxy group to a ketone, comprising:
conducting the conversion in the presence of a catalyst system;
the catalyst system comprising:
a noble metal and
a metal oxide, wherein the catalyst system is selected from the group of systems consisting of system I, system II and system III,
wherein
the noble metal is at least one selected from the group consisting of ruthenium, rhodium, palladium, osmium, iridium and platinum,
in system I the noble metal is unsupported and the metal oxide comprises at least one of titanium dioxide and zirconium dioxide;
in system II the noble metal is supported, the noble metal support does not comprise titanium dioxide or zirconium dioxide, and the system further comprises at least one of titanium dioxide and zirconium dioxide; and
in system III the noble metal is supported on zirconium dioxide as the metal oxide.

9. A process for synthesizing a lactam, comprising:
preparing a ketone according to the process of claim 1;
oximating the ketone to obtain a ketoximine; and
treating the ketoxime to effect a Beckmann rearrangement and form the lactam.

10. The process according to claim 9, wherein the compound E is 1,2-cyclododecane epoxide.

* * * * *